United States Patent
Nakano et al.

(10) Patent No.: US 8,337,601 B2
(45) Date of Patent: Dec. 25, 2012

(54) AIR FILTER SHEET, PROCESS FOR MANUFACTURING SAME, AND AIR FILTER

(75) Inventors: Toshiro Nakano, Yokohama (JP); Satoshi Minobe, Yokohama (JP); Takashi Tanahashi, Yokohama (JP)

(73) Assignee: Nichias Corporation, Tokyo (JP)

(*) Notice: Subject to any disclaimer, the term of this patent is extended or adjusted under 35 U.S.C. 154(b) by 1332 days.

(21) Appl. No.: 11/339,482

(22) Filed: Jan. 26, 2006

(65) Prior Publication Data

US 2006/0185336 A1 Aug. 24, 2006

(30) Foreign Application Priority Data

Feb. 16, 2005 (JP) .................. 2005-039321

(51) Int. Cl.
*B01D 53/02* (2006.01)
(52) U.S. Cl. ............... 96/134; 55/524; 96/135; 96/154
(58) Field of Classification Search ............ 55/524; 95/285; 96/134–135, 154
See application file for complete search history.

(56) References Cited

U.S. PATENT DOCUMENTS

| | | | | |
|---|---|---|---|---|
| 4,127,706 A * | 11/1978 | Martin et al. | ........... | 429/122 |
| 4,153,661 A * | 5/1979 | Ree et al. | ........... | 264/120 |
| 4,194,040 A * | 3/1980 | Breton et al. | ........... | 428/325 |
| 4,906,378 A * | 3/1990 | Hagen et al. | ........... | 210/635 |
| 5,071,610 A * | 12/1991 | Hagen et al. | ........... | 264/120 |
| 5,204,376 A * | 4/1993 | Henmi et al. | ........... | 521/32 |
| 5,482,906 A * | 1/1996 | Sakai et al. | ........... | 502/402 |
| 5,891,402 A * | 4/1999 | Sassa et al. | ........... | 422/171 |
| 6,146,451 A * | 11/2000 | Sakata et al. | ........... | 96/135 |
| 6,224,655 B1 * | 5/2001 | Messier | ........... | 96/226 |
| 6,402,819 B1 * | 6/2002 | De Ruiter et al. | ........... | 96/153 |
| 7,077,891 B2 * | 7/2006 | Jaffe et al. | ........... | 96/108 |
| 2003/0158309 A1 * | 8/2003 | Ono et al. | ........... | 524/261 |

FOREIGN PATENT DOCUMENTS

| | | |
|---|---|---|
| JP | 07-194921 | 8/1995 |
| JP | 11-178905 | 7/1999 |
| JP | 2003-082217 | 3/2003 |
| JP | 2003-220333 | * 8/2003 |
| JP | 2003-300066 | 10/2003 |
| KR | 10-0385598 | 8/2003 |

OTHER PUBLICATIONS

Office Action issued Jan. 20, 2012, in Korean Patent Application No. 10-2006-0014193 with English Translation.

* cited by examiner

*Primary Examiner* — Duane Smith
*Assistant Examiner* — Ives Wu
(74) *Attorney, Agent, or Firm* — Oblon, Spivak, McClelland, Maier & Neustadt, L.L.P.

(57) ABSTRACT

An air filter sheet comprising particles of a functional agent with an average particle diameter of 0.1 to 30 μm and fibrils of a polytetrafluoroethylene resin with a number average molecular weight of 3,000,000 to 50,000,000, the ratio by weight of the functional agent to the fibrils of the polytetrafluoroethylene resin being from 1 to 99. According to the present invention, an air filter sheet comprising fibrils of polytetrafluoroethylene resin with a functional agent carried thereon, possessing excellent formability, and being free from a lubricant, a process for manufacturing the air filter sheet, and an air filter free from contamination of outgas with a lubricant are provided.

20 Claims, 3 Drawing Sheets

US 8,337,601 B2

AIR FILTER SHEET, PROCESS FOR MANUFACTURING SAME, AND AIR FILTER

BACKGROUND OF THE INVENTION

1. Field of the Invention

The present invention relates to an air filter used for removing ionized gaseous pollutants, total organic compound (TOC), moisture, ozone, and other foreign matter with an abnormal odor from the air in clean rooms and the like, an air filter sheet for manufacturing the air filter, and a method for manufacturing the same. More particularly, the present invention relates to an air filter possessing aeration cavities and carrying a functional agent, a sheet for manufacturing the air filter, and a process for manufacturing the same.

2. Background Art

In frontier industries such as the semiconductor manufacturing industry and liquid crystal display manufacturing industry, controlling pollution of the air and product surfaces in clean rooms to prevent pollution is important to ensure a high yield, high quality, and reliability of the products. In the semiconductor manufacturing industry, in particular, as the degree of integration of the products increases, control of ionized gaseous pollutants, TOC, moisture, ozone, and other foreign matters with an abnormal odor has become indispensable in addition to the control of particulate matter using a HEPA filter, a ULPA filter, and the like.

The ionized gaseous pollutants include basic gases and acidic gases. Of these gases, ammonia, which is a basic gas, is known to adversely affect developability during the step of exposure to radiation and to cause wafer surfaces to become clouded in the manufacture of semiconductors. $SO_X$, which is an acidic gas, produces lamination defects in substrates in a thermal oxidation membrane-forming step during manufacture of semiconductors, whereby the characteristics and reliability of the semiconductor devices are adversely affected.

Since ionized gaseous pollutants cause various problems in semiconductor manufacturing processes and the like, the concentration of ionized gaseous pollutants in a clean room used in semiconductor manufacturing and the like is required to be reduced to several micron grams per cubic meter ($\mu g/m^3$).

For this reason, air filters made from a fibrous carrier with aeration cavities, which carries an ion-exchanger as a functional agent, have been conventionally used for removing ionized gaseous materials. A conventionally used air filter will be described referring to FIG. 5. FIG. 5 is a schematic diagram showing a conventional air filter with aeration cavities. The air filter 20 shown in FIG. 5 is fabricated by inserting an ion-exchange resin-carrying fiber material 25, which is obtained by causing an ion-exchanger to be carried on a fibrous carrier formed by alternately laminating a corrugated fiber 21 and a flat fiber 22, into a frame 26. Aeration cavities 23 are formed between the corrugated fiber 21 and the flat fiber 22. Gas to be processed 27 is caused to pass through the air filter 20 in the air flow direction 24, whereby ionized gaseous pollutants in the gas to be processed 27 is adsorbed on the filter and removed. In this instance, the direction in which the aeration cavities 23 are formed is parallel to the air flow direction 24.

Moisture must be removed, because the moisture participates in the formation of oxide films which cause wafer malfunctions. To remove moisture, an air filter carrying a dehumidification agent has been used. Ozone generated in an apparatus in a clean room operated at a high voltage must also be removed, because the ozone produces an oxide film on wafers. To remove ozone, an air filter carrying an ozone decomposition catalyst has been used.

In the above air filter, the functional agent such as an ion-exchanger is carried by an inorganic or organic binder. To cause the functional agent to be carried on a fibrous carrier, the carrier must be impregnated with a slurry prepared by mixing the functional agent with a binder, or such a slurry must be attached to the fibrous carrier. An excess amount of the binder may cover the surface of the functional agent carried on the fibrous carrier, impairing the adsorption performance of the air filter.

Since the above air filter is demanded not only to exhibit excellent initial removing performance, but also to maintain the excellent initial removing performance for a long period, in other words, to possess outstanding durability, the air filter must carry a large amount of functional agent thereon.

To this end, the surface area of the fibrous carrier material on which the functional agent is carried must be increased by increasing the number of aeration cavities per unit volume of the air filter. To increase the number of aeration cavities the cross-section area of openings of the aeration cavities must be decreased. However, if the cross-section area of one aeration cavities is too small, the slurry cannot enter the aeration cavities during the operation of carrying the functional agent on the fibrous material or the functional agent may clog the aeration cavities.

This problem can be solved if the functional agent can be carried on an air filter without using a binder.

As the method for causing the functional agent to be carried without using a binder, a method of using a polytetrafluoroethylene resin in the form of fibril (hereinafter referred to from time to time as "fibrillated polytetrafluoroethylene resin") and causing the polytetrafluoroethylene resin to capture the substance to be carried has been used. For example, JP-A-2003-220333 discloses an ammonia gas capturing composite material comprising a solid capturing material capable of capturing the ammonia gas and a fibrillated polytetrafluoroethylene resin. The solid capturing material is held by the polytetrafluoroethylene resin so that ammonia gas is capable of reaching the solid capturing material, whereas a liquid is incapable of reaching the solid capturing material.

JP-A-2003-300066 discloses a composite powdery material for capturing ammonia gas comprising an ammonia gas capturing powder covered with a polytetrafluoroethylene resin having a number average molecular weight of 200,000 to 2,000,000.

In the manufacture of conventional air filters in which a functional agent is captured by a fibrillated polytetrafluoroethylene resin such as the composite capturing material described in JP-A-2003-220333, the fibrillated polytetrafluoroethylene resin is prepared by applying a shearing stress to a polytetrafluoroethylene resin. However, when applying a shearing stress to a polytetrafluoroethylene resin in this method, fibrils of the fibrillated polytetrafluoroethylene resin are vigorously entangled with each other to produce lumps if a lubricant such as a solvent naphtha is not added. Therefore, mixing a lubricant is essential. For this reason, conventional air filters contain a lubricant.

However, if an air filter contains a lubricant, the lubricant mixes in the air passing through the air filter (hereinafter referred to from time to time as "outgas"), thereby polluting the outgas. Since even a very small amount of lubricant in the air may affect the product quality when the air is used in clean rooms particularly for manufacturing semiconductors, liquid-crystals, and the like, air filters containing a lubricant cannot be used.

JP-A-2003-300066 states that a polytetrafluoroethylene resin having a molecular weight in the range of 200,000 to 2,000,000 can be fibrillated without adding a lubricant. However, a sheet obtained from such a polytetrafluoroethylene resin is too tender due to the small molecular weight to maintain a configuration (such as a corrugate) of the air filter when formed into that configuration. Therefore, the sheet possesses only very poor shape retainability.

An object of the present invention is therefore to provide an air filter sheet comprising fibrils of polytetrafluoroethylene resin with a functional agent carried thereon, possessing excellent formability, and being free from contamination of outgas with a lubricant, and a process for manufacturing the sheet. Another object of the present invention is to provide an air filter formed from the sheet comprising fibrils of polytetrafluoroethylene resin with a functional agent carried on the fibers, being free from contamination with a lubricant.

As a result of extensive studies to solve the above problems in the conventional technologies, the inventors of the present invention have discovered that if particles of a functional agent with a specific particle size are added to particles of a polytetrafluoroethylene resin, the polytetrafluoroethylene resin can be excellently fibrillated without using a lubricant, because the functional agent acts as a lubricant in the mixture.

SUMMARY OF THE INVENTION

Specifically, the present invention provides a sheet for an air filter (air filter, sheet) comprising particles of a functional agent with a particle diameter of 0.1 to 30 μm and fibrils of a polytetrafluoroethylene resin with a number average molecular weight of 3,000,000 to 50,000,000, the ratio by weight of the functional agent to the fibrils of the polytetrafluoroethylene resin being from 1 to 99.

The present invention further provides a process for manufacturing an air filter sheet comprising a fibrillation step of providing a mixture (A) comprising particles of a functional agent with a particle diameter of 0.1 to 30 μm and particles of a polytetrafluoroethylene resin with a number average molecular weight of 3,000,000 to 50,000,000 at a ratio by weight of the functional agent to the polytetrafluoroethylene resin particles of 1 to 99 and applying a shearing stress to the component (A) to obtain a mixture (B) of the functional agent and fibrils of the polytetrafluoroethylene resin, and a rolling step of rolling the mixture (B) while applying a sharing stress to obtain the air filter sheet.

The present invention still further provides an air filter having aeration cavities obtainable from the above air filter sheet.

The air filter of the present invention exhibits high adsorption capability due to a large amount of a functional agent carried without using a binder. In addition, because the air filter can be manufactured without using a lubricant, the outgas is not contaminated with a lubricant. The process for manufacturing the air filter of the present invention excels in formability and can manufacture the air filter sheet without using a lubricant.

DETAILED DESCRIPTION OF THE PRESENT INVENTION AND PREFERRED EMBODIMENTS

The air filter sheet of the present invention contains particles of a functional agent and fibrils of polytetrafluoroethylene resin.

Figure 1:
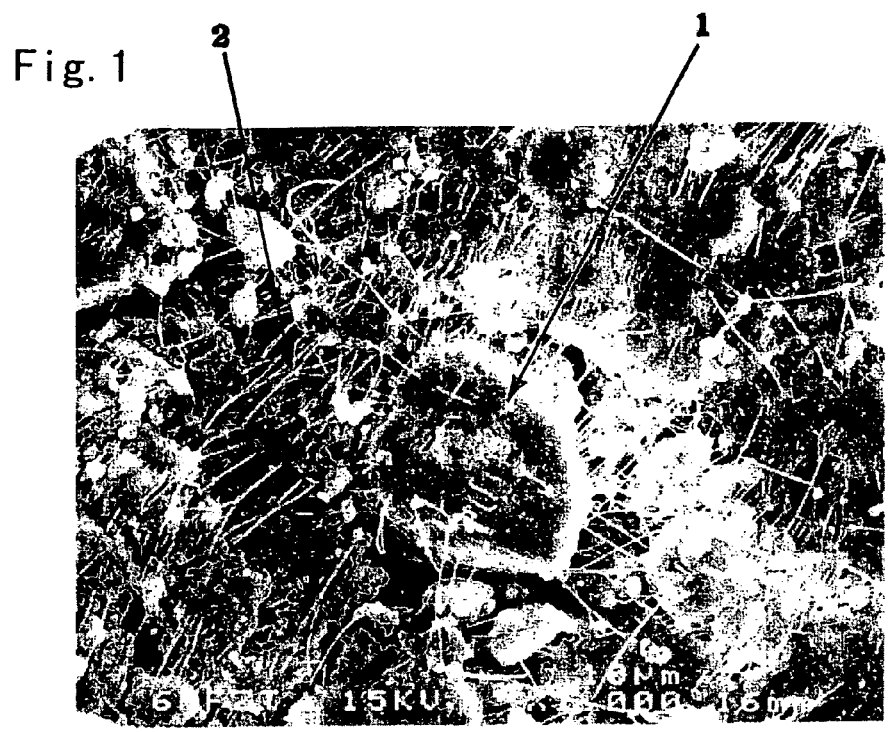
FIG. 1 is an SEM photograph of the surface of air filter sheet of the present invention.

An embodiment of the air filter sheet will be described referring to FIG. 1. FIG. 1 shows an SEM photograph of the surface of an air filter sheet containing ion-exchanger particles and fibrils of polytetrafluoroethylene resin (hereinafter referred to from time to time as "PTFE resin"). In FIG. 1, 1 is an ion-exchange resin and 2 indicates fibrils of PTFE resin. As shown in FIG. 1, the fibrils of PTFE resin 2 have a very thready needle-like shape and the ion-exchanger particles 1 are held by three-dimensional networks formed by the fibrils of PTFE resin 2. In this manner, the functional agent can be carried on the air filter sheet without using an inorganic or organic binder. Since the fibrils of PTFE resin are very thin, the functional agent can be retained in the network of the fibrils of PTFE resin in the state in which almost all particle surfaces are exposed without being covered with the fibrils.

There are no specific limitations to the type of the functional agent used. Any functional agents used in air filters for adsorbing ionized gaseous pollutants, organic solvents, moistures, and odors, for decomposing ozone, or the like can be used. For example, an ion-exchange resin, activated carbon, zeolite, silica gel, metal oxide catalyst, and the like can be given.

The ion-exchange resin used as the functional agent in the present invention is mainly of the type used for removing ionized gaseous pollutants. The ion-exchange resin may be either a cation-exchange resin or an anion-exchange resin, or a combination of a cation-exchange resin and an anion-exchange resin. As the type of cation-exchange resin used in the present invention, a strongly acidic cation-exchange resin can be given, for example. As the type of anion-exchange resin used in the present invention, a strongly basic anion-exchange resin can be given, for example.

The ion-exchange resin has an ion-exchange capacity usually from 1 to 10 meq/g, and preferably 3 to 6 meq/g. If the ion-exchange capacity is less than 1 meq/g, the ion-exchange resin exhibits only insufficient reactivity with ionized gaseous pollutants and its performance in removing the ionized gaseous pollutants tends to decrease. If the ion-exchange capacity is more than 10 meq/g, the ion-exchange resin has only poor chemical stability and the ion-exchange groups tend to be released from the ion-exchange resin.

When the gas to be processed contains both a basic gas (ammonia, amines, etc.) and an acidic gas ($SO_X$, $NO_X$, etc.), the ion-exchange resin preferably contains both a cation-exchange resin and an anion-exchange resin because of the capability of removing both the basic gas and acidic gas.

When the ion-exchange resin contains both the cation-exchange resin and anion-exchange resin, the mixing ratio by weight is from 99:1 to 1:99. If the mixing ratio is outside of the range of 99:1 to 1:99, the reactivity of either the cation-exchange resin or anion-exchange resin with ionized gaseous pollutants tends to decrease.

The activated carbon used as the functional agent in the present invention is mainly the functional agent used for TOC removal, ozone decomposition, and the like. According to the raw material type, the activated carbon includes activated carbon made from wood, activated carbon made from coal, activated carbon made from coconut, and the like. Any type may be used in the present invention without specific limitations. The activated carbon commonly called "impregnated carbon" which contains an inorganic salt such as potassium carbonate added thereto may also be used. Among these, coconut activated carbon is preferable due to the good balance of performance and price. When used for removing TOC, activated carbon with a large specific surface area and a large pore volume is preferable. For decomposing ozone, impregnated carbon is preferable.

Zeolite used as the functional agent includes a hydrophilic type and a hydrophobic type. The hydrophilic type zeolite is an adsorbent mainly used for removing ionized gaseous pollutants, deodorization, and the like. The hydrophobic type zeolite is an adsorbent mainly used for removing TOC, deodorization, and the like. Zeolite obtained by synthesis usually contains sodium as counter ion in the acid point. Zeolite with part or all of the sodium ions replaced with other metal ions, sodium-removed zeolite, aluminum-removed zeolite, and the like may also be used.

Zeolite with various crystal structures such as A-type zeolite, X-type zeolite, Y-type zeolite, β-type zeolite, mordenite, ferrielite, ZSM-5, and the like can be given. Of these, A-type zeolite, X-type zeolite, Y-type zeolite, and ZSM-5 are preferable due to the low price.

The silica gel used as the functional agent in the present invention is mainly that used for dehumidification. Examples of the silica gel include, but are not limited to, A-type silica gel, B-type silica gel, and the like.

The metal oxide catalysts used as the functional agent in the present invention is mainly those used for ozone decomposition, deodorization, and the like. Examples of the metal oxide catalyst include, but are not limited to, manganese oxide, cobalt oxide, copper oxide, a mixed catalyst of manganese oxide-copper oxide, a mixed catalyst of manganese oxide-cobalt oxide, titanium oxide, and the like. On the surface of the metal oxide-catalyst, malodorous substances such as triethylamine and methylmercaptan are deodorized by decomposition, and ozone is oxidized into oxygen molecules.

The average particle diameter of the functional agent is from 0.1 to 30 μm, and preferably from 1 to 20 μm. If the average particle diameter of the functional agent is less than 0.1 μm, particles of the functional agent easily drop out from the air filter sheet; if more than 30 μm, the lubricating effect of the functional agent during manufacture of the air filter sheet decreases. Therefore, it is difficult to manufacture an air filter sheet in which the functional agent particles with an average particle diameter of more than 30 μm are captured by fibrils of PTFE.

The fibrils of polytetrafluoroethylene resin can be obtained by applying a shearing stress to particles of polytetrafluoroethylene resin. The method of producing polytetrafluoroethylene fibrils by applying a shearing stress to a polytetrafluoroethylene resin has conventionally been employed. The process of producing fibrils is called "fibrillation."

The number average molecular weight of the polytetrafluoroethylene resin is from 3,000,000 to 50,000,000, and preferably from 5,000,000 to 15,000,000. If the number average molecular weight of the polytetrafluoroethylene resin is less than 3,000,000, the air filter sheet is too tender to obtain an air filter with good shape retainability after forming. It is difficult to manufacture air filters with a corrugated honeycomb structure, for example. An air filter sheet can be excellently formed by using a polytetrafluoroethylene resin having a number average molecular weight of more than 50,000,000. It is, however, difficult to obtain a polytetrafluoroethylene resin having a number average molecular weight of more than 50,000,000, because commercially available polytetrafluoroethylene resins usually have a number average molecular weight of 50,000,000 or less.

The ratio by weight of the functional agent to the fibrils of polytetrafluoroethylene resin is from 1 to 99, preferably from 4 to 32, and particularly preferably from 9 to 19. If the ratio by weight of the functional agent to the fibrils of polytetrafluoroethylene resin is less than 1, performance of the air filter such as adsorption performance tends to decrease; if more than 99, the strength of the air filter sheet is impaired or the functional agent tends to easily drop out from the air filter sheet.

Although there are no specific limitations, the thickness of the air filter sheet is preferably from 0.05 to 1 mm, and particularly preferably from 0.1 to 0.5 mm. For example, in the case of an air filter formed by alternately laminating a corrugated air filter sheet and a flat air filter sheet, the smaller the thickness of the air filter sheet, the larger the number of the sheet laminated to obtain a specific height, which results in an increased number of aeration cavities formed per unit volume of air filter and a large surface area per unit volume of air filter. Therefore, a small thickness of the air filter sheet is preferable to obtain an air filter having high adsorption performance. However, if the thickness is less than 0.05 mm, the strength of the air filter sheet is inadequate. On the other hand, if the thickness is more than 1 mm, the number of aeration cavities formed per unit volume of air filter decreases.

Although there are no specific limitations, the amount of the functional agent carried per unit area of the air filter sheet is preferably from 100 to 600 g/m$^2$, and particularly preferably from 200 to 500 g/m$^2$.

Due to the manufacturing process in which no lubricant is used, the air filter sheet of the present invention does not contain a lubricant. Therefore, if gas is processed by using the air filter formed from the air filter sheet of the present invention, the gas passing through the air filter does not contain a lubricant. On the other hand, in the manufacture of conventional air filter sheets, since a liquid organic compound such as solvent naphtha, alcohol, isoper, or thinner is used as a lubricant in fibrillation of polytetrafluoroethylene resin, the conventional air filter sheets contain a lubricant. Therefore, if gas is processed by using the air filter formed from the conventional air filter sheet, the gas passing through the air filter contains a lubricant, which may cause serious problems in the manufacturing processes, particularly in the manufacturing processes of semiconductors and liquid crystals.

In addition, since the air filter sheet of the present invention is made from fibrils of high molecular weight polytetrafluoroethylene resin with a number average molecular weight of 3,000,000 to 50,000,000, the air filter sheet exhibits excellent shape retainability after forming.

In the manufacture of the air filter of the present invention, after the fibrillation step, a rolling step is carried out.

In the fibrillation step, a shearing stress is applied to a mixture (A) containing particles of the functional agent and polytetrafluoroethylene resin to obtain a mixture (B) of the functional agent and fibrils of polytetrafluoroethylene resin.

There are no specific limitations to the type of functional agent used in the fibrillation step. Any functional agents commonly used in air filters can be used. An adsorbent of ionized gaseous pollutants, adsorbent of organic solvents, dehumidification agent, deodorant, and the like can be given as examples. The description of the functional agent used in the fibrillation step is omitted insofar as the description of the functional agent used for the air filter sheet of the present invention can be applied, and different features will now be described.

The average particle diameter of the functional agent is from 0.1 to 30 μm, preferably from 1 to 25 μm, and particularly preferably from 10 to 20 μm. Because the functional agent with an average particle diameter in the above range can function as a lubricant when particles of polytetrafluoroethylene resin are fibrillated by applying a shearing stress, even a high molecular weight polytetrafluoroethylene resin with a number average molecular weight of 3,000,000 to 50,000,000 can be excellently fibrillated without adding a lubricant. If the average particle diameter of the functional agent is less than 0.1 μm, particles of the functional agent easily drop out from the air filter sheet during or after the rolling step. If more than 30 μm, it is difficult for the functional agent to function as a lubricant, producing lumps of polytetrafluoroethylene resin or a mixture of polytetrafluoroethylene resin and functional agent when a shearing stress is applied. The lubricating effect of the functional agent thus decreases.

The description on the type and the number average molecular weight of polytetrafluoroethylene resin particles used in the fibrillation step is omitted, because they are the same as those in the air filter sheet of the present invention.

The average particle diameter of the polytetrafluoroethylene resin particles is from 300 to 500 μm. Particles commonly called "fine powder" are preferable.

The mixture (A) used in the fibrillation step contains the functional agent and particles of polytetrafluoroethylene resin. The ratio by weight of the functional agent to the particles of polytetrafluoroethylene resin in the mixture (A) is from 1 to 99, preferably from 4 to 32, and particularly preferably from 9 to 19. If the ratio by weight of the functional agent to the particles of polytetrafluoroethylene resin is less than 1, performance of the air filter sheet or air filter such as adsorption performance is low; if more than 99, the strength of the air filter sheet is impaired. As required, the mixture (A) may contain a reinforcing agent and the like.

A shearing stress is applied to this mixture (A) to fibrillate the polytetrafluoroethylene resin particles. In the fibrillation step according to the present invention, particles of polytetrafluoroethylene resin can be excellently fibrillated without adding a lubricant to the mixture (A), when applying a shearing stress to the mixture (A). Since the lubricant referred to herein is the same as that used for the above air filter sheet of the present invention, the description is omitted.

There are no specific limitations to the method of applying a shearing stress to the mixture (A). For example, a method of stirring the mixture (A) using a Henschel mixer, a method of grinding using a mortar, and the like can be given.

Although there are no specific limitations, the temperature when applying a shearing stress to the mixture (A) is preferably from 50 to 150° C., and particularly preferably from 80 to 120° C. There are also no specific limitations to the time for which a shearing stress is applied to the mixture (A) insofar as the time is sufficiently long for fibrillation to occur. Preferably, the shearing stress is applied to for 1 to 60 minutes, and particularly preferably for 3 to 30 minutes.

As a specific example of the fibrillation step, a method of adding the functional agent and particles of polytetrafluoroethylene resin to a mixing vessel and shaking the vessel or stirring the mixture in the vessel using a stirrer by which no shearing stress is applied to the mixture to obtain a mixture (A), and adding the mixture (A) to a Henschel mixer or the like to apply a shearing stress to the mixture (A) can be given, for example.

A mixture of the functional agent and polytetrafluoroethylene resin in which the former is dispersed in fibrils of the latter (hereinafter referred to from time to time as "mixture (B)") can be obtained by performing the fibrillation step.

Because the functional agent can function as a lubricant when the polytetrafluoroethylene resin is fibrillated in the fibrillation step, even a high molecular weight polytetrafluoroethylene resin with a number average molecular weight of 3,000,000 to 50,000,000 can be excellently fibrillated without adding a lubricant.

Next, the mixture (B) is rolled while applying a shearing stress in the rolling step. The mixture (B) is formed into a sheet in the rolling step, whereby the thickness of the fibril of polytetrafluoroethylene resin is further reduced. Since the area of the functional agent covered by the fibrils is reduced by reducing the thickness of the fibril of polytetrafluoroethylene resin in this manner, the adsorption performance and the like of the air filter is increased.

The method for rolling the mixture (B) is not specifically limited and includes a method commonly employed in the manufacture of resin sheets, such as a method of using a kneader, a method of using a calendar roll, a method of using an extruding machine, and the like. Although the temperature during rolling the mixture (B) is not specifically limited, the temperature is usually from 50 to 150° C., and preferably from 80 to 120° C.

In the rolling step, the rolling operation of the mixture (B) may be carried out either one time or two or more times to obtain an air filter sheet with a desired thickness. Specifically, a sheet obtained by rolling may be again rolled. Rolling the mixture (B) two or more times, particularly 3 to 10 times, is preferable for obtaining an air filter sheet with high strength.

The mixture (B) may be a formed material such as pellets produced by using an extruding press machine, for example. Specifically, the mixture (B) obtained by the fibrillation step may be formed into pellets, which are used in the rolling step.

Since the air filter sheet obtained in the rolling step comprises fibrils of high molecular weight polytetrafluoroethylene resin with a number average molecular weight of 3,000,000 to 50,000,000, the air filter sheet exhibits excellent shape retainability. Therefore, the air filter sheet can be suitably used for producing an air filter having a corrugated honeycomb structure, for example. In addition, the process of the present invention for manufacturing the air filter sheet can be suitably applied to the manufacture of the aforementioned air filter sheet of the present invention.

The air filter of the present invention has aeration cavities and can be obtained by forming the above air filter sheet of the present invention. For example, such an air filter can be obtained by alternately laminating a flat air filter sheet of the present invention and a corrugated air filter sheet of the present invention formed into a waveform, or by alternately laminating a flat air filter sheet of the present invention and a pleated air filter sheet of the present invention formed into a pleated form. The structure obtained by alternately laminating a flat air filter sheet and a corrugated air filter sheet formed into a waveform is commonly referred to as a corrugated honeycomb structure.

Figure 2:
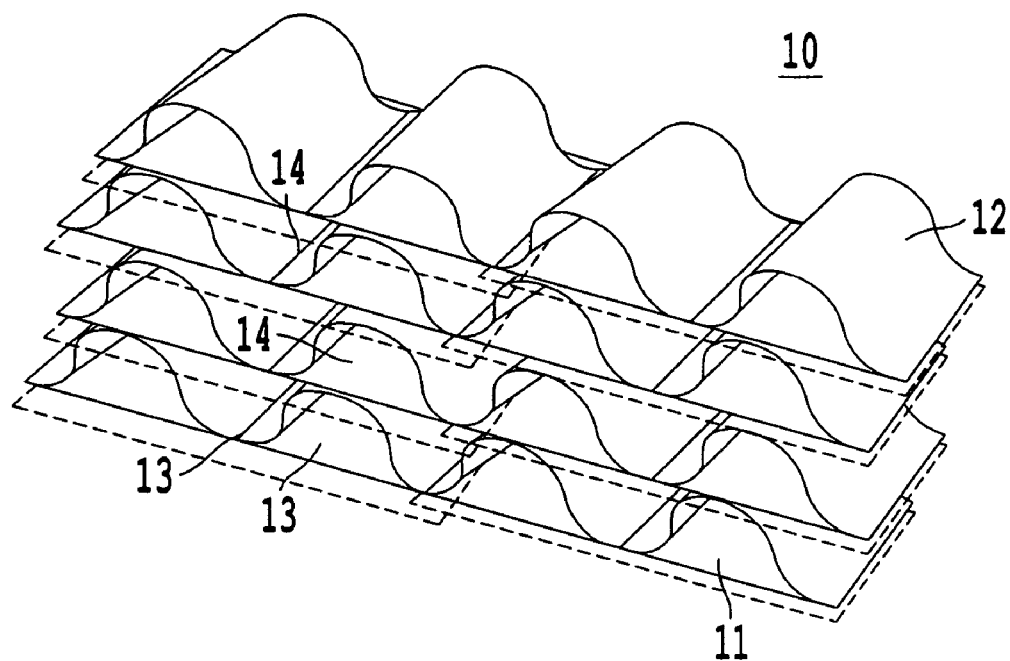
FIG. 2 is a perspective view schematically showing an embodiment of the air filter of the present invention.
Figure 3:
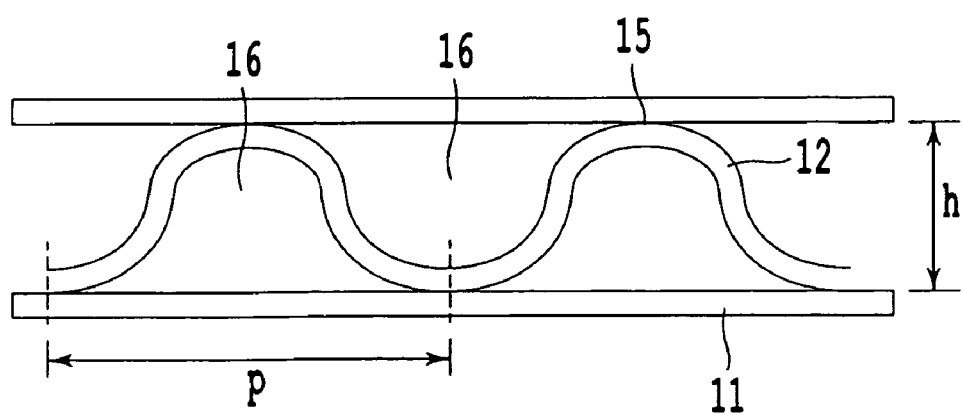
FIG. 3 is a schematic cross-section of the air filter shown in FIG. 2 cut along the plane perpendicular to the air flow direction.
Figure 5:
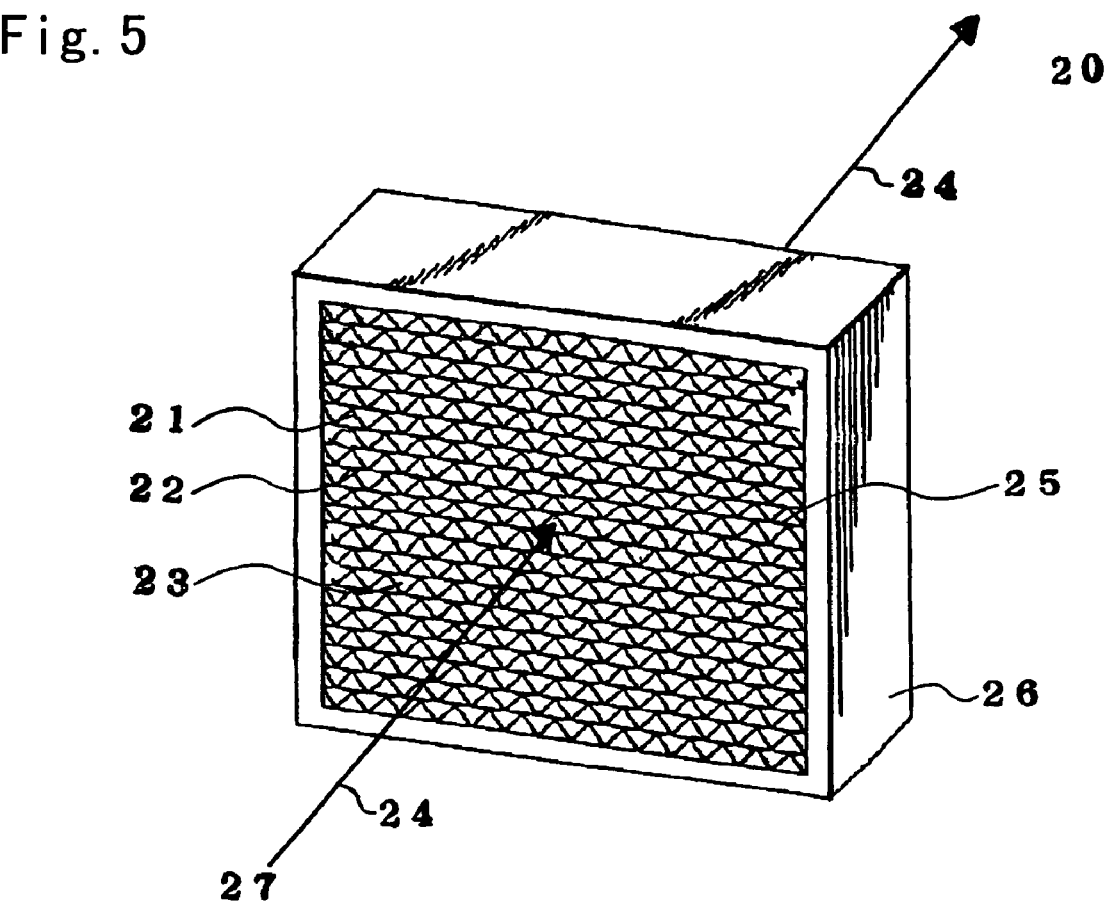
FIG. 5 is a schematic diagram showing a conventional air filter with aeration cavities.

The air filter will now be described by referring to FIG. 2 and FIG. 3. FIG. 2 is a perspective view schematically showing an embodiment of the air filter of the present invention. FIG. 3 is a schematic cross-section of the air filter 10 cut along a plane perpendicular to the air flow direction. The air filter 10 has a corrugated honeycomb structure made from alternately laminated flat air filter sheets 11 and corrugated air filter sheets 12. Between the corrugated air filter sheet 12 and two flat air filter sheets 11, 11 located on the bottom and top of the corrugated air filter sheet 12, there are formed nearly half-cylindrical aeration cavities 13, 13 extending in the direction of the continuous upper and lower ridges 15, 15 of the corrugated air filter sheet 12. The air to be processed is introduced from openings 14 and passed through the aeration cavities 13.

The corrugated air filter sheet 12 is formed by corrugating the flat air filter sheet 11. Corrugating is a process for fabricating a flat sheet material such as the flat air filter sheet 11 into a waveform object by passing the flat air filter sheet through a pair of upper and lower corrugating rolls.

The flat air filter sheet 11 and the corrugated air filter sheet 12 are alternately laminated using the corrugated air filter sheet 12 as a center core to obtain the air filter 10. The flat air filter sheet 11 and the corrugated air filter sheet 12 can be caused to adhere to each other at the upper and lower ridges 15, 15 of the corrugated air filter sheet 12 (center core) by applying a small force to the extent of slightly pressing them each other. The two air filter sheets may be caused to adhere by using a binder. As examples of the binder, inorganic binders such as colloidal silica, and organic binders such as an acrylic binder and vinyl acetate binder can be given. In addition, a laminate of the two air filter sheets prepared by simply layering them without pressing, and placed and secured in a frame or the like may also be used.

The number of the openings 16 existing in the cross-section of the air filter 10 in the direction perpendicular to the air flow direction is from 1 to 160/cm$^2$, preferably from 30 to 150/cm$^2$, and particularly preferably from 50 to 140/cm$^2$. The larger the number of the openings 16, the larger the number of aeration cavities 13 per unit volume of the air filter 10 and the larger the surface area per unit volume of the air filter 10, whereby the performance of the air filter 10 such as adsorption performance increases. However, if the number of the openings 16 exceeds the above range, the area of the openings is unduly decreased, resulting in a large pressure loss of the air to be processed.

Although there are no specific limitations, the height of the ridge (h in FIG. 3) of the air filter 10 is preferably from 0.5 to 5 mm, and particularly preferably from 0.7 to 4 mm. Although there are also no specific limitations, the pitch of the air filter 10 (p in FIG. 3) is preferably from 1.5 to 10 mm, and particularly preferably from 1.8 to 5 mm.

The amount of the functional agent carried per unit volume of the air filter is usually from 100 to 700 kg/m$^3$, and preferably from 300 to 600 kg/m$^3$.

Since the air filter contains a great amount of functional agent per unit volume, which is carried without using a binder, the air filter exhibits excellent performance such as adsorption performance. In addition, since the polytetrafluoroethylene resin forming the filter has a high molecular weight, the air filter possesses excellent shape retainability.

EXAMPLES

The present invention will be described in more detail by examples, which should not be construed as limiting the present invention.

Example 1

(Preparation of Air Filter Sheet)

A strongly acidic cation-exchange resin ("Diaion" manufactured by Mitsubishi Chemical Corp., ion-exchange capacity: 5 meq/g, average particle diameter: 0.3 mm) was ground and classified to obtain an ion-exchange resin (A) having an average particle diameter of 20 μm. On the particle size distribution curve of the ion-exchange resin (A), D50 was 20.5 μm. After drying at 110° C., the ion-exchange resin (A) was cooled in a nitrogen atmosphere. Next, 95 parts by weight of the cooled ion-exchange resin (A) and 5 parts by weight of polytetrafluoroethylene resin (PTFE) with a number average molecular weight of 12,000,000 ("Fine Powder" manufactured by Du Pont-Mitsui Fluorochemicals Co., LTD.) were put into a vessel, which was shaken for five minutes to obtain a mixture (A1). After heating at 110° C., a shearing stress was applied to the mixture (A1) using a Henschel mixer at 3,000 rpm for five minutes to obtain a mixture (B1) of the ion-exchange resin (A) and the fibril of polytetrafluoroethylene resin.

The mixture (B1) was formed into pellets with a diameter of 10 mm and a thickness of about 50 mm using an extruding press machine. The pellets were rolled at 110° C. three times using a calendar roll to obtain a flat air filter sheet (A) with a thickness of 0.25 mm. In this instance, pellets with a diameter of 10 mm were formed into a sheet with a thickness of 5 mm in the first rolling, which was rolled into a sheet with a thickness of 1 mm in the second rolling. Then, the sheet with a thickness of 0.25 mm was produced from the sheet with a thickness of 1 mm in the third rolling operation. The resulting flat air filter sheet (A) contained the ion-exchange resin in an amount of 305 g/m$^2$ and possessed a tensile strength of 0.1 kgf/mm$^2$.

(Preparation of Air Filter)

The flat air filter sheet (A) was caused to pass through a pair of waveform corrugators to obtain a corrugated air filter sheet (A). After applying an acrylic binder to the ridge parts of the corrugated air filter sheets (A) as an adhesive, the flat air filter sheets (A) were superposed and laminated. The corrugated air filter sheet (A) and the flat air filter sheet (A) were laminated in turn so that the air passages were aligned in the same direction. The laminate was cut into a piece with a length of 120 mm, width of 120 mm, and a thickness of 40 mm, to obtain an air filter (A) having a corrugated honeycomb structure as shown in FIG. 2 and FIG. 3 with a center core pitch (p in FIG. 3) of 2.5 mm and a ridge height (h in FIG. 3) of 1.1 mm. The air filter (A) contained the ion-exchange resin in an amount of 414 kg/m$^3$, possessed an ion-exchange capacity per unit volume of 2,419 eq/m$^3$, and contained 73 openings 16 per cm$^2$.

(Evaluation)

Figure 4:
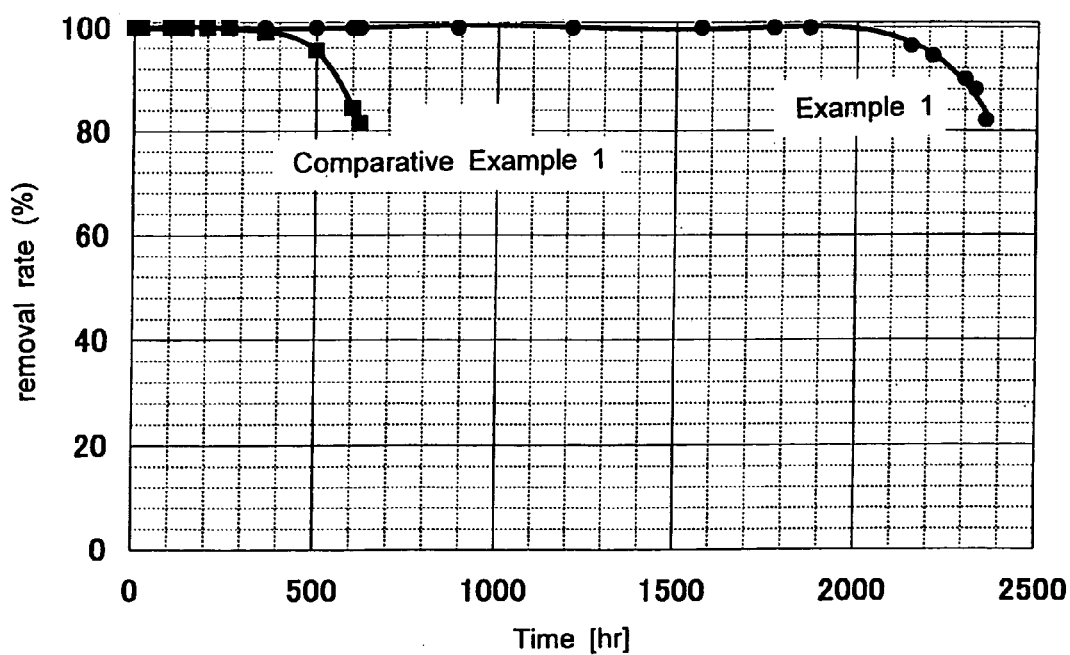
FIG. 4 is a graph showing the change over time of the ammonia gas removal rate.

The change in the ammonia removal rate over time and the life of the air filter (A) were measured under the following conditions. Although the ammonia concentration causing problems in a clean room in practice is in the order of several μg/m$^3$, an ammonia concentration of 340 μg/m$^3$ was used in the accelerated test. The results are shown in FIG. 4. The life of the air filter (A) determined as the time required for the ammonia removal rate of the air filter to decrease to 90% was 2,300 hours. The pressure loss of the air filter (A) determined under these conditions was 30 Pa.

(Test Conditions)
   Composition of feed gas: air containing 340 μg/m$^3$ of ammonia
   Temperature and humidity of the feed gas: 23° C., 50% RH
   Target gas to be removed: ammonia
   Gas feed rate: 0.5 m/sec (Measurement of Amount of Organic Compound Mixed in Outgas Passing Through Air Filter)

The amount of organic compounds mixed in the outgas passing through the air filter (A) obtained according to the above method was measured under the following conditions. As a result, the total amount of detected organic compounds was 1.4 μg/m$^3$.

(Test Conditions)
   Composition of feed gas: clean air
   Temperature and humidity of the feed gas: 23° C., 50% RH
   Gas feed rate: 0.5 m/sec (Method of Sampling of Outgas)
  Sample collection tube: TENAX
  Suction rate: 1.0 l/min.
  Suction time: 30 minutes starting from 24 hours after initiation of feed
  Analytical instrument: GC-MS Comparative Example 1

(Preparation of Fibrous Carrier with Corrugated Honeycomb Structure)

A flat fiber sheet (B) (silica alumina fiber, thickness: 0.2 mm) was caused to pass through a pair of waveform corrugators to obtain a corrugated fiber sheet (B). After applying silica sol to the ridge parts of the corrugated fiber sheet (B) as an adhesive, the flat fiber sheets (B) were superposed and laminated. The corrugated fiber sheet (B) and the flat fiber sheet (B) were laminated in turn in a manner so that the air passages were aligned in the same direction. The resulting product was cut into a square with dimensions of 120 mm×120 mm with a thickness of 40 mm, thereby obtaining a fibrous carrier (B) having a corrugated honeycomb substrate as shown in FIG. 2 and FIG. 3 with a center core pitch (p in FIG. 3) of 2.8 mm and a ridge height (h in FIG. 3) of 1.3 mm.

(Preparation of Air Filter)

A slurry containing ion-exchange resin powder was prepared from the ion-exchange resin (A) used in Example 1, and silica sol ("SNOWTEX" manufactured by Nissan Chemical Industries, Ltd., solid content: 20 wt %) and water used as a binder. The ratio by weight of the ion-exchange resin (A) to the solid components of silica sol was 8:2 and the total amount of the ion-exchange resin (A) and the solid components of silica sol in the slurry was 30 wt %. A fibrous carrier (B) having the corrugated honeycomb structure was dipped in the slurry in a container for 60 seconds and, after removing from the slurry, was dried at 80° C. for 60 minutes to cause the ion-exchange resin (A) to be carried on the fibrous carrier, thereby obtaining an air filter (B). The amount of ion-exchange resin carried on the air filter (B) was 100 kg/m$^3$, the ion-exchange capacity per unit volume was 500 eq/m$^3$, and the number of openings 16 was 54/cm$^2$.

(Evaluation)

The change in the ammonia removal rate over time and the life of the air filter (B) were measured under the same conditions as in Example 1. The results are shown in FIG. 4. The life of the air filter (B) was 560 hours.

Comparative Example 2

(Preparation of Fibrous Carrier with Corrugated Honeycomb Structure)

A fibrous carrier was prepared in the same manner as in Comparative Example 1, except that the center core pitch was 2.5 mm instead of 2.8 mm, and the ridge height was 1.1 mm instead of 1.3 mm.

(Preparation of Air Filter)

An air filter was prepared using the same method as in Comparative Example 1, except for using the above fibrous carrier as the fibrous carrier to be dipped in the slurry. There were a number of clogged aeration cavities observed in the obtained air filter.

Comparative Example 3

(Application of Slurry to Fibrous Carrier)

The slurry obtained in Comparative Example 1 was applied to a flat fiber sheet (C) (silica alumina fiber, thickness: 0.2 mm) using a roll coater and dried at 80° C. for 60 minutes, thereby causing the ion-exchange resin (A) to be carried on the flat fiber sheet (C) (first coating). A second coating was carried out in the same manner using the slurry to obtain a flat fiber sheet (C) with ion-exchange resin carried thereon. The amount of ion-exchange resin carried on the flat fiber sheet (C) was 131 g/m$^2$.

(Preparation of Air Filter)

An air filter sheet (C) was obtained in the same manner as in Example 1, except for using the flat fiber sheet (C) with the ion-exchange resin carried thereon instead of the flat air filter sheet (A) and applying silica sol as an adhesive instead of the acrylic binder. The amount of ion-exchange resin carried on the air filter (C) was 147 kg/m$^3$, the ion-exchange capacity per unit volume was 750 eq/m$^3$, and the number of openings 16 was 54/cm$^2$.

Comparative Example 4

(Application of Slurry to Fibrous Carrier)

A flat fiber sheet (C) with ion-exchange resin carried thereon was obtained in the same manner as in Comparative Example 3.

(Preparation of Air Filter)

An air filter sheet (D) was obtained in the same manner as in Example 1, except that the flat fiber sheet (C) with the ion-exchange resin carried thereon was used instead of the flat air filter sheet (A), silica sol was applied as an adhesive instead of the acrylic binder, the center core pitch was 2.2 mm instead of 2.8 mm, and the ridge height was 1.0 mm instead of 1.3 mm. The amount of ion-exchange resin carried on the air filter (D) was 163 kg/m$^3$, the ion-exchange capacity per unit volume was 815 eq/m$^3$, and the number of openings 16 was 54/cm$^2$.

Comparative Example 5

(Application of Slurry to Fibrous Carrier)

The slurry obtained in Comparative Example 1 was applied to a flat fiber sheet (E) (silica alumina fiber, thickness: 0.35 mm) using a roll coater and dried at 80° C. for 60 minutes, thereby causing the ion-exchange resin (A) to be carried on the flat fiber sheet (E) (first coating). A second coating and third coating were carried out in the same manner using the slurry to obtain the flat fiber sheet (E) with ion-exchange resin carried thereon. The amount of ion-exchange resin carried on the flat fiber sheet (E) was 195 g/m$^2$.

(Preparation of Air Filter)

An air filter (E) was obtained in the same manner as in Example 1, except for using the flat fiber sheet (E) with ion-exchange resin carried thereon instead of the flat air filter sheet (A) and applying silica sol as an adhesive instead of the acrylic binder. The amount of ion-exchange resin carried on the air filter (E) was 203 kg/m$^3$, the ion-exchange capacity per unit volume was 1,015 eq/m$^3$, and the number of openings 16 was 54/cm$^2$.

Comparative Example 6

(Application of Slurry to Fibrous Carrier)

A flat fiber sheet (E) with ion-exchange resin carried thereon was obtained in the same manner as in Comparative Example 5.

(Preparation of Air Filter)

An air filter sheet (F) was obtained in the same manner as in Example 1, except that the flat fiber sheet (E) with ion-exchange resin carried thereon was used instead of the flat air filter sheet (A), silica sol was applied as an adhesive instead of the acrylic binder, the center core pitch was 2.2 mm instead of 2.8 mm, and the ridge height was 1.0 mm instead of 1.3 mm. The amount of ion-exchange resin carried on the air filter (F) was 207 kg/m$^3$, the ion-exchange capacity per unit volume was 1,035 eq/m$^3$, and the number of openings 16 was 54/cm$^2$.

Example 2

(Preparation of Air Filter Sheet)
An air filter sheet (A) was obtained in the same manner as in Example 1.
(Preparation of Air Filter)
An air filter (G) was prepared in the same manner as in Example 1, except that the center core pitch was 2.2 mm instead of 2.5 mm, and the ridge height was 1.0 mm instead of 1.1 mm. The amount of ion-exchange resin carried on the air filter (G) was 457 kg/m$^3$, the ion-exchange capacity per unit volume was 2,670 eq/m$^3$, and the number of openings 16 was 92/cm$^2$.
Evaluation
The air filter (G) was evaluated in the same manner as in Example 1 to confirm that the life of the filter was 3,000 hours. The pressure loss of the air filter determined under these conditions was 45 Pa.

Comparative Example 7

(Preparation of Air Filter Sheet)
An air filter sheet (H) was prepared in the same manner as in Example 1, except that 5 parts by weight of a polytetrafluoroethylene resin with a number average molecular weight of 1,000,000 was used instead of 5 parts by weight of the polytetrafluoroethylene resin with a number average molecular weight of 12,000,000.
(Preparation of Air Filter)
The air filter sheet (H) obtained was subjected to a waveform corrugator to find that the corrugated formed product instantly regained the original flat shape. No corrugated air filter sheet was obtained. Therefore, an air filter was not also produced.

Comparative Example 8

(Preparation of Air Filter Sheet)
The same experiment as in Example 1 was carried out, except that 95 parts by weight of a strongly acidic cation-exchange resin (B) ("Diaion" manufactured by Mitsubishi Chemical Corp.) with an average particle diameter of 100 μm was used instead of 95 parts by weight of the ion-exchange resin (A) with an average particle diameter of 20 μm. Due to clumping of the mixture of the ion-exchange resin and PTFE, an air filter sheet could not be produced.

Comparative Example 9

(Preparation of Air Filter Sheet)
The strongly acidic cation-exchange resin used in Example 1 was ground and classified to obtain an ion-exchange resin (C) having an average particle diameter of 100 μm. After drying at 110° C., the ion-exchange resin (C) was cooled in a nitrogen atmosphere. Next, 95 parts by weight of the cooled ion-exchange resin (C) and 5 parts by weight of the polytetrafluoroethylene resin used in Example 1 were put into a vessel, which was shaken for five minutes to obtain a mixture (C1). After heating at 110° C., the mixture was put into a Henschel mixer, followed by the addition of 20 parts by weight of hydrocarbon extrusion adjuvant ("Isoper E" manufactured by Exxon Mobile Corp.). A shearing stress was applied to the mixture at 3,000 rpm for five minutes to obtain a mixture (D1) of the ion-exchange resin (C) and the fibrils of polytetrafluoroethylene resin. Then, the same procedure as in example 1 was followed, except for using the mixture (D1) instead of the mixture (B1), to obtain a flat air filter sheet (J) with a thickness of 0.25 mm.
(Preparation of Air Filter)
An air filter (J) was prepared in the same manner as in Example 1, except for using an air filter sheet (J) instead of the air filter sheet (A).
(Measurement of Amount of Organic Compound Mixed in Outgas Passing Through Air Filter)
The same experiment in Example 1 was carried out, except for using the air filter (J) instead of the air filter (A), to confirm that the total amount of organic compounds detected was 630 μg/m$^3$.
As a result of measuring the amount of organic compounds mixed in the outgas passing through the air filter, it was confirmed that the air filter (A) of Example 1 does not cause the problem of outgas contamination in clean rooms, based on the extremely small total amount of organic compounds of 1.4 μg/m$^3$ detected in the outgas. On the other hand, the total organic compounds of 630 μg/m$^3$ detected in the outgas passing through the air filter (J) of Comparative Example 9 indicates that the air filter (J) cannot be used for a clean room.

TABLE 1

|  | Example | | Comparative Example | | |
| --- | --- | --- | --- | --- | --- |
|  | 1 | 2 | 1 | 2 | 3 |
| Properties and performance of air filter | | | | | |
| Thickness of sheet (mm) | 0.25 | 0.25 | — | — | — |
| Thickness of fiber sheet (mm) | — | — | 0.2 | 0.2 | 0.2 |
| Pitch p (mm) | 2.5 | 2.2 | 2.8 | 2.5 | 2.5 |
| Ridge height h (mm) | 1.1 | 1.0 | 1.3 | 1.1 | 1.1 |
| Amount of ion-exchange resin carried per unit volume (kg/m$^3$) | 414 | 457 | 100 | — | 147 |
| Ion-exchange | 2,419 | 2,670 | 500 | — | 750 |

TABLE 1-continued

|  | Example | | Comparative Example | | |
| --- | --- | --- | --- | --- | --- |
|  | 1 | 2 | 1 | 2 | 3 |
| capacity per unit volume (eq/m³) | | | | | |
| Life (h) | 2,300 | 3,000 | 560 | — | — |
| Amount of organic compound in outgas (μg/m³) | 1.4 | — | — | — | — |
| Remarks | — | — | Ion-exchange capacity is small. Life is short. | There were a number of clogged cavities. | Ion-exchange capacity is small. |

TABLE 2

|  | Comparative Example | | | | |
| --- | --- | --- | --- | --- | --- |
|  | 4 | 5 | 6 | 7 | 8 |
| Properties and performance of air filter | | | | | |
| Thickness of sheet (mm) | — | — | — | — | — |
| Thickness of fiber sheet (mm) | 0.2 | 0.35 | 0.35 | — | — |
| Pitch p (mm) | 2.2 | 2.5 | 2.2 | — | — |
| Ridge height h (mm) | 1.0 | 1.1 | 1.0 | — | — |
| Amount of ion-exchange resin carried per unit volume (kg/m³) | 163 | 203 | 207 | — | — |
| Ion-exchange capacity per unit volume (eq/m³) | 815 | 1,015 | 1,035 | — | — |
| Life (h) | — | — | — | — | — |
| Amount of organic compound in outgas (μg/m³) | — | — | — | — | — |
| Remarks | Ion-exchange capacity is small. | Ion-exchange capacity is small. | Ion-exchange capacity is small. | Corrugated air filter sheet could not be formed. | Air filter sheet could not be produced. |

TABLE 3

| Properties and performance of air filter | Comparative Example 9 |
| --- | --- |
| Thickness of sheet (mm) | 0.25 |
| Thickness of fiber sheet (mm) | — |
| Pitch p (mm) | 2.5 |
| Ridge height h (mm) | 1.1 |
| Amount of ion-exchange resin carried per unit volume (kg/m³) | — |
| Ion-exchange capacity per unit volume (eq/m³) | — |
| Life (h) | — |
| Amount of organic compound in outgas (μg/m³) | 630 |
| Remarks | Amount of organic compound in outgas is large. |

What is claimed is:

1. An air filter sheet comprising:
one or more particles of at least one functional agent selected from the group consisting of an ion-exchange resin, an activated carbon, a zeolite, and a silica gel, wherein the functional agent has an average particle diameter of from 0.1 μm to 30 μm; and
one or more fibrils of a fibrillated polytetrafluoroethylene resin having a number average molecular weight of from 3,000,000 to 50,000,000,
wherein a weight ratio of the functional agent to the fibrillated polytetrafluoroethylene resin is from 1 to 99, and
wherein the air filter sheet does not comprise a lubricant,
wherein the air filter sheet is produced by a process comprising:
performing fibrillation in a dry state in the absence of a lubricant by applying a shearing stress to a mixture (A) to obtain a mixture (B),
wherein the mixture (A) comprises the functional agent and a particulate polytetrafluoroethylene resin having a number average molecular weight of from 3,000,000 to 50,000,000, wherein the weight ratio of the functional agent to the particulate polytetrafluoroethylene resin is from 1 to 99, and
wherein the mixture (B) comprises the functional agent and the fibrillated polytetrafluoroethylene resin; and rolling the mixture (B) while applying a shearing stress to obtain the air filter sheet.

2. The air filter sheet according to claim 1, wherein the functional agent is an ion-exchange resin.

3. The air filter sheet according to claim 1, wherein the functional agent is an ion-exchange resin having an ion-exchange capacity of 1-10 meq/g.

4. The air filter sheet according to claim 1, wherein the functional agent is a cation-exchange resin.

5. The air filter sheet according to claim 1, wherein the functional agent is an anion-exchange resin.

6. The air filter sheet according to claim 1, wherein the functional agent is an activated carbon.

7. The air filter sheet according to claim 1, wherein the functional agent is a zeolite.

8. The air filter sheet according to claim 1, wherein the functional agent is a hydrophilic zeolite.

9. The air filter sheet according to claim 1, wherein the functional agent is a hydrophobic zeolite.

10. The air filter sheet according to claim 1, wherein the functional agent is a silica gel.

11. The air filter sheet according to claim 1, wherein the functional agent has an average particle diameter of from 1 μm to 25 μm.

12. The air filter sheet according to claim 1, wherein the functional agent has an average particle diameter of from 10 μm to 20 μm.

13. The air filter sheet according to claim 1, wherein the particulate polytetrafluoroethylene resin has an average particle diameter of from 300 μm to 500 μm.

14. The air filter sheet according to claim 1, wherein the weight ratio of the functional agent to the fibrillated polytetrafluoroethylene resin is from 4 to 32.

15. The air filter sheet according to claim 1, wherein the weight ratio of the functional agent to the fibrillated polytetrafluoroethylene resin is from 9 to 19.

16. The air filter sheet according to claim 1, wherein the amount of the functional agent carried per unit area of the air filter is from 100 $g/m^2$ to 600 $g/m^2$.

17. The air filter sheet according to claim 1, wherein the amount of the functional agent carried per unit area of the air filter is from 200 $g/m^2$ to 500 $g/m^2$.

18. The air filter sheet according to claim 1, wherein the amount of the functional agent carried per unit volume of the air filter is from 100 $kg/m^3$ to 700 $kg/m^3$.

19. The air filter sheet according to claim 1, wherein the amount of the functional agent carried per unit volume of the air filter is from 300 $kg/m^3$ to 600 $kg/m^3$.

20. The air filter sheet according to claim 1, which has a corrugated honeycomb structure.

* * * * *